(12) United States Patent
Giovanetti et al.

(10) Patent No.: US 7,365,226 B2
(45) Date of Patent: Apr. 29, 2008

(54) PROCESS FOR THE PURIFICATION OF GABAPENTIN

(75) Inventors: Roberto Giovanetti, Schio (IT); Andrea Nicoli, Vicenza (IT); Angelo Restelli, Gerenzano (IT); Livius Cotarca, Cervignano del Friuli (IT)

(73) Assignee: Zach System S.p.A., Bresso, Milan (IT)

( * ) Notice: Subject to any disclaimer, the term of this patent is extended or adjusted under 35 U.S.C. 154(b) by 0 days.

(21) Appl. No.: 10/582,790

(22) PCT Filed: Dec. 14, 2004

(86) PCT No.: PCT/EP2004/053470

§ 371 (c)(1),
(2), (4) Date: Jun. 14, 2006

(87) PCT Pub. No.: WO2005/058797

PCT Pub. Date: Jun. 30, 2005

(65) Prior Publication Data

US 2007/0123590 A1    May 31, 2007

(30) Foreign Application Priority Data

Dec. 16, 2003  (IT) .......................... MI2003A2456

(51) Int. Cl.
*C07C 61/08*    (2006.01)
(52) U.S. Cl. ..................................... 562/507

(58) Field of Classification Search ................ None
See application file for complete search history.

(56) References Cited

U.S. PATENT DOCUMENTS

2004/0068011 A1*  4/2004  Cannata et al. ............. 514/561
2007/0123590 A1   5/2007  Giovanetti et al.

FOREIGN PATENT DOCUMENTS

WO           02/34709       5/2002

OTHER PUBLICATIONS

"Ion Exachange" in Kirk-Othmer Encyclopedia of Chemical Technology, Copyright © 1995 by John Wiley & Sons, pp. 1-50.*
U.S. Appl. No. 10/593,813, filed Sep. 22, 2006, Giovanetti et al.
U.S. Appl. No. 10/582,790, filed Jun. 14, 2006, Giovanetti et al.
U.S. Appl. No. 10/582,790, filed Jun. 14, 2006, Glovanetti et al.
U.S. Appl. No. 10/561,018, filed Dec. 16, 2005, Cotarca et al.
U.S. Appl. No. 11/722,056, filed Jun. 18, 2007, Giovanetti et al.

* cited by examiner

*Primary Examiner*—Karl Puttlitz
(74) *Attorney, Agent, or Firm*—Oblon, Spivak, McClelland, Maier & Neustadt, P.C.

(57) ABSTRACT

A process for the preparation of gabapentin comprising the passage of a salt of the same through a ionic exchange resin of strong cationic type, the elution of the gabapentin which has fixed onto the column and the crystallization from organic solvent, characterized in that the resin is regenerated by using a mineral acid in a molar quantity between 50 and 90%, is described.

24 Claims, No Drawings

PROCESS FOR THE PURIFICATION OF GABAPENTIN

The present invention relates to a process for the purification of gabapentin.

Gabapentin (The Merck Index, XII Ed., page 733, No. 4343), is a known drug with anti-epileptic and anticonvulsant activity described for the first time in the U.S. Pat. No. 4,024,175 in the name of Warner-Lambert Co.

In the literature several processes for the preparation of gabapentin have been described (for example the U.S. Pat. Nos. 4,024,175, 5,068,413 and 5,091,567).

Substantially, all these processes provide a final purification stage by means of column chromatography of an aqueous solution of a gabapentin salt, generally the hydrochloride, on an ionic exchange resin of weak basic type.

In the PCT patent application WO 02/34709, in the name of the same Applicant, instead, a gabapentin purification process has been described providing the treatment of an aqueous solution of gabapentin hydrochloride on ionic exchange resins characterized in that the ionic exchange resins are of the strong cationic type.

The process described in the PCT patent application mentioned above is very effective and allows obtaining, after concentrating the eluate and crystallization, a product with high purity, almost completely exempted from the corresponding lactam which is a substance provided with a certain toxicity (Von A. Enders et al., Arzneimittel Forschung, vol. 10, 1960, 243-250).

During the step of chromatography on cationic resin gabapentin fixes onto the resin by leaving percolating the other substances, in particular organic impurities deriving from the synthetic process.

Gabapentin is then eluted with an ammoniacal aqueous solution and then with water.

The fractions containing gabapentin are collected and concentrated under vacuum until obtaining a solid residue therefrom gabapentin is isolated by crystallization from organic solvents, preferably alcohols.

The process described above results to be optimum with reference to the gabapentin purification.

Nevertheless, said process by considering the various steps which usually characterize a chromatographic process such as, for example, the column feeding, the product elution, the washings and the regeneration of the utilized resins, requires a huge quantity of eluants.

Then, upon examining the purification in detail through the ionic exchange resin it is possible noting that the process, in a way inherent to the common procedure of industrial implementation, takes a long time and produces a considerable quantity of scraps.

By way of example, by referring to the industrial process described in the patent application mentioned above, for a gabapentin charge of about 350 kg of crystallized end product, a great quantity of eluants is utilized, about 11900 l thereof for the resin regeneration step alone.

Of course, this involves a particular effort for the scrap disposal plant.

Furthermore, by considering that the solutions are fed to the plant with a speed of about 2000 l/hour, it is possible realizing the time necessary to carry out the whole process.

Consequently, it is necessary to study alternative methodologies allowing implementing the process in reduced times and under conditions allowing limiting the quantity of the produced scraps.

Now we have surprisingly found an improvement in the process described in the patent application WO 02/34709 allowing to considerably reducing the quantity of scraps by providing at the same time a pure product as well and with substantially identical yields.

In particular, the use of ionic exchange resins in the industrial processes provides that after the elution step one provides in the regeneration treatment of the resin from the salified form.

Therefore, regenerating means making the resins reusable in a subsequent purification cycle after that the elution step, necessary to release the gabapentin bound to the resin, has ended, Generally, the regeneration of strong cationic resins is carried out by using an aqueous solution of an inorganic acid followed by the washing with demineralized water.

Usually the resin producer itself shows which acids are the most appropriate for the regenerating treatment, but as a general rule strong mineral acids such as, for example, hydrochloric, nitric and sulfiric acid, are used.

The number of moles of acid in aqueous solution which are introduced into the column during the regeneration step is decided based upon the utilized molar quantity of cationic resin, which is upon the effective capacity thereof generally expressed in eq./l.

Generally, the acid/resin molar ratios are equal to a fair excess with respect to the theoretical one (1:1) in order to activate the exchange sites of the whole resin and then to restore the efficiency. According to the producers, for a complete regeneration an acid/resin ratio around 2.6/1 is necessary. For regeneration equal to about 90-95% (the one usually utilized in the plants) a 1.5/1 acid/resin ratio is sufficient.

By means of the subsequent washing with demineralized water the column is again ready to be used.

Said improvement in the process described in the PCT patent application mentioned above in the name of the same Applicant consists in using in the regeneration step of the strong cationic exchange resin a reduced quantity of aqueous solution of inorganic acid with respect to the theoretical one, which could be defined beater, equal to a fair percentage of the resin moles, so as to activate an initial part of the resin in column.

The gabapentin salt upon eluting meets a first part of activated resin and upon fixing to the column releases the remaining acid necessary to the regeneration of the not previously activated resin fraction.

Of course, in order to avoid the direct contact and the consequent mixing between the beater and the solution of the gabapentin salt fed in column, during the charging step it could be useful interposing between the two solutions a minimum quantity of demineralized water. Its quantity depends upon the plant geometry and at industrial level it can be approximately estimated in a quantity between 50 l and 200 l.

Therefore, object of the present invention is a process for the preparation of gabapentin comprising the passage of a salt of the same through a ionic exchange resin of the strong cationic type, the elution of the gabapentin which has fixed onto the column and the crystallization from organic solvent, characterized in that the regeneration of the ionic exchange resin of strong cationic type is carried out:

a. by partially regenerating the resin through a beater constituted by an aqueous solution of inorganic acid in a quantity equal to a percentage of the resin moles comprised between 50 and 90%;

b. by adding demineralized water in a quantity sufficient to separate the beater from the solution of a gabapentin salt of item c.;

c. by adding a solution of a gabapentin salt and by completing the resin regeneration through the acid released by the fixing of the gabapentin salt to the resin itself;
d. by eluting the gabapentin which has fixed to the resin by using a base.

Not limitative examples of strong cationic resins which can be used in the invention process are IRA120, DIAION SK1B and IMAC HP 1110.

Not limitative examples of inorganic acids utilized in the regeneration process of ionic exchange resins of strong cationic type of the present invention are hydrochloric, nitric and sulfuric acid.

Preferably the inorganic acid utilized in the partial regeneration process of the ionic exchange resin of strong cationic type is the acid corresponding to the anion of the gabapentin addition salt which has to be purified.

Basically for reasons of costs, in the common industrial practice the gabapentin hydrochloride intermediate is usually used.

In the present invention, therefore, there is described in detail the case wherein the gabapentin salt is the hydrochloride and the regeneration process of the used resins is carried out with an aqueous solution of hydrochloric acid.

As it will be clear to the person skilled in the art the regeneration of ionic exchange resins of the strong cationic type, deriving from the purification process of other gabapentin salts, according to the process of the present invention, can be carried out by replacing the hydrochloric acid with adequate quantities of the acid corresponding to the chosen anion of the gabapentin salt.

The partial regeneration of the ionic exchange resin of the strong cationic type is carried out by utilizing an aqueous solution of inorganic acid in a quantity equal to a percentage of resin moles preferably around 70-80%.

Preferably the partial regeneration is carried out with an aqueous solution of hydrochloric acid.

Preferably a solution of hydrochloric acid with a concentration comprised between 5 and 10% is utilized and still more preferably with a concentration around 6%.

In the process object of the present invention the gabapentin elution step from the column is carried out through conventional techniques preferably by column feeding with an ammonia aqueous solution, preferably with a concentration equal or less 4%, according to what described in the patent application WO 02/34709.

An additional preferred elution methodology of the gabapentin which has fixed to the strong cationic resin provides the use of an ammonia aqueous solution and alkaline hydroxide according to what described in the co-pending International patent application No. PCT/EP2004/006513 in the name of the same Applicant filed on 17 Jun. 2004. Generally, the utilized alkaline hydroxide is, for reasons of costs, sodium hydroxide with a concentration preferably around 7% in weight. The concentration of the ammonia solution is around 3-4% in weight and the molar ratio between ammonia and sodium hydroxide is preferably comprised between 1:1 and 1:2.

A second object of the present invention is a process for the preparation of gabapentin comprising the passage of gabapentin hydrochloride through a ionic exchange resin of strong cationic type, the elution of the gabapentin which has fixed onto the column, the concentration and crystallization from organic solvent, characterized in that the regeneration of the ionic exchange resin of strong cationic type is carried out:

a. by partially regenerating the resin through a beater constituted by an aqueous solution of hydrochloric acid in quantities equal to a percentage of resin moles comprised between 50 and 90%;
b. by adding demineralized water in a quantity sufficient to separate the beater from the solution of gabapentin hydrochloride of item c.;
c. by adding a solution of gabapentin hydrochloride and by completing the resin regeneration through the hydrochloric acid released by fixing the gabapentin hydrochloride to the resin itself;
d. by eluting the gabapentin which has fixed to the resin by using a base.

Furthermore, a third object of the present invention is a regeneration process of a strong cationic exchange resin used in the purification of a gabapentin salt comprising:
a. the partial regeneration through a beater constituted by an aqueous solution of inorganic acid in a quantity equal to a percentage of resin moles comprised between 50 and 90%;
b. the addition of demineralized water in a quantity sufficient to separate the beater from the solution of a gabapentin salt of item c.;
c. the addition of a solution of a gabapentin salt and the completion of the resin regeneration through the acid released by fixing the gabapentin salt to the resin itself.

Practically, the regeneration methodology object of the invention allows considerably reducing the quantity of eluants used in the gabapentin synthesis process.

This translates into a significant reduction in the time necessary to carry out the process and in the scrap disposal costs.

Thus, for example, if with the methodology described in the patent application WO 02/34709, about 5100 l of aqueous solution of 6% hydrochloric acid and about 6800 l demineralized water were necessary, for a total of about 11900 l of eluants in the resin regeneration step by each 350 Kg of produced gabapentin, with the methodology object of the present invention for the same gabapentin quantity about 3800 l of an aqueous solution of 6% hydrochloric acid and about 50 l of demineralized water for a total of about 3850 l are sufficient.

Furthermore, as it has been reminded previously, considering that the solutions are fed in the plant at about 2000 l/hour, about 4 working hours for each gabapentin salt charge are saved on the average.

In a practical embodiment the process object of the invention comprises the partial regeneration of a strong cationic exchange resin from the salified form with a quantity of an aqueous solution of inorganic acid around 70-80% in moles with respect to the theoretical one, the addition of separating demineralized water, the addition of a solution of a gabapentin salt, the gabapentin fixing onto the resin, the washing with water, the elution with an ammonia solution and then with water by collecting the fractions containing gabapentin, the concentration of the fractions by distillation until obtaining a dense residue therefrom the gabapentin is isolated by crystallization from alcoholic solvents according to known methods.

In an alternative embodiment the process object of the invention comprises the partial regeneration of a strong cationic exchange resin from the salified form with a quantity of an aqueous solution of inorganic acid around 70-80% in moles with respect to the theoretical one, the addition of separating demineralized water, the addition of a solution of a gabapentin salt, the gabapentin fixing onto the resin, the washing with water, the resin elution with an aqueous solution of ammonia and sodium hydroxide and the resin washing with demineralized water, the collection of the fractions containing gabapentin, the solution concentration until about 50%, the neutralization with HCl of the existing gabapentin sodium salt, the additional concentration until a dense residue, the gabapentin crystallization from alcoholic solvents according to known methods.

In order to better illustrate the present invention the following examples are now provided.

EXAMPLE 1

In a glass column (diameter 45 mm, height 450 mm) equipped with porous septum, containing 500 ml of Diaion SK1B resin (effective capacity 2.2 eq./l) in the salified form, that was not regenerated, 468.0 g of a 6% solution of hydrochloric acid (equal to 0.77 moles, that was 70% of the resin moles) were eluted at a speed of 2 Bv/h (1 l/h).

At the end 50.0 g of demineralized water were further eluted.

A solution of gabapentin hydrochloride (652 g of 14.48% solution equal to 94.4 g of gabapentin) was fed into the column.

Subsequently it was washed with approximately 1500 g of demineralized water until pH 7.

Then the product was eluted with an ammonia solution and was crystallized according to what described in the patent application WO 02/34709 by obtaining gabapentin with a yield and purity comparable to the ones obtained through a regeneration methodology carried out according to conventional techniques.

EXAMPLE 2

In a glass column (diameter 45 mm, height 450 mm) equipped with porous septum, containing 500 ml of Diaion SK1B resin (effective capacity 2.2 eq./l) in the salified form, that was not regenerated, 468.0 g of a 6% solution of hydrochloric acid (equal to 0.77 moles, that was 70% of the resin moles) were eluted at a speed of 2 Bv/h (1 l/h).

At the end 50.0 g of demineralized water were further eluted.

A solution of gabapentin hydrochloride (652 g of 14.48% solution equal to 94.4 g of gabapentin) was fed into the column.

Subsequently it was washed by eluting with approximately 1500 g of demineralized water until pH 7.

Then a mixture (720 g) of 3% ammoniacal solution (240 g) and a 7% solution of NaOH (480 g) were fed into the column.

At the end demineralized water until pH 7 (about 1500 g) was fed.

The eluate fractions containing gabapentin were gathered by obtaining a solution (2171 g) containing gabapentin (4.25%, 92.3 g).

23.4 g of HCl 3.99% solution (equal to 0.934 g of HCl) were added thereto.

The solution was then vacuum-concentrated at a temperature lower than 40° C. by obtaining a crude residue (91.2 g) containing 97.6% gabapentin.

Crude gabapentin (70 g), demineralized water (34.7 g) and methanol (43.7 g) were charged in a 500 ml reactor under nitrogen.

The suspension was heated at 50° C. for 30 minutes, then isopropanol (180.5 g) was dropped in 30 minutes.

The mixture was kept at 50° C. for further 30 minutes, then it was cooled at 25° C. in 2 hours and at −5° C. in an additional hour, by keeping it at this temperature for further 2 hours.

The solid was filtered and washed onto the filter with isopropanol cooled at −5° C. After drying in oven at 45° C., gabapentin (64 g) with purity higher than 99% was obtained.

EXAMPLE 3

In C104 and C105 columns, connected in series (containing about 150 l of IMAC HP 1110 resin under not regenerated form), were charged in equicurrent, with a flow of about l/h 150, in the order about 164 kg of about 6% solution of hydrochloric acid (equal to 81% of the resin moles) and, subsequently, 15 kg of demineralized water and, subsequently, a solution of gabapentin hydrochloride constituted by 150.2 kg of demineralized water and 33.8 kg of 100% gabapentin hydrochloride.

Once ended the elution of the gabapentin hydrochloride solution the columns were fed with about 400 kg of demineralized water until Bx=0÷0.3 and pH≈7.

About 243 kg of 3% ammonia were eluted in equicurrent onto the columns, with a flow of about 150 l/h.

Subsequently with the same modes about 414 kg of demineralized water were eluted.

With the refractometer the Bx course of the solution coming out from the columns was followed and 3 portions of eluate were collected, the first one with BX=0 until Bx started to rise, the second one starting from the moment wherein Bx started to rise until when, after reaching a maximum Bx of about 20, it decreased again to 2 and the third one with Bx=2 until Bx of 0.2÷0.3.

In a reactor the second elution fraction was charged (until Bx 2).

About 0.92 kg (0.8 l) of sint. hydrochloric acid were added to the solution.

The solution was concentrated by vacuum-distillation without exceeding the inner temperature of 40° C. until obtaining a semi-solid residue.

Then, 17.4 kg (22.1 l) of methanol were charged. They were heated at about 50° C. for 30 minutes, then by keeping the temperature at about 50° C., in about 30 minutes 72.2 kg (92,0 l) of isopropanol were added.

It was kept at about 50° C. for 30 minutes, it was cooled at about 20° C. in 2 hours, then it was cooled at −5° C. After about 1 hour at about −5° C. it was centrifuged in ID401 in one or more stages. The product was washed for three times with a total of 21.4 kg (27.2 l) of isopropanol at 0° C.

23.6 kg of gabapentin (yield 84%), titre=100.2%, lactam=0.01%, chlorides=80 ppm, total impurities=0.05% was obtained.

EXAMPLE 4

In a glass column (diameter 45 mm, height 450 mm) charged with 500 ml of Diaion SK1B resin (total exchange capacity 2.2 eq./l) in the salt form (not regenerated), 602 g of a 6% solution of hydrochloric acid (0.77 eq. corresponding to 70% of exchange resin moles) were eluted at a 2Bv/h flow (1 l/h).

At the end the resin was washed with 50 g of demi water and then a gabapentin sulfate solution (800 g having gabapentin=9.6%, corresponding to 76.8 g) was charged at the same elution rate.

The resin was washed until pH 6-7 with approximately 1500 g of demineralized water.

Then, the product was eluted with 643 g of a 3% ammonia solution, followed by approximately 1550 g of demineralized water to wash the resin until neutrality.

The recovery of gabapentin from elution solution and the crystallization of the product was performed according to what described in the PCT patent application n. WO 02/34709 by obtaining gabapentin with a yield and purity comparable to the ones obtained through a regeneration methodology carried out according to conventional techniques.

EXAMPLE 5

In a glass column (diameter 45 mm, height 450 mm) charged with 500 ml of Diaion SK1B resin (total exchange capacity 2.2 eq./l) in the salt form (not regenerated), 471 g of a 8% solution of sulfuric acid (0.77 eq. corresponding to 70% of exchange resin moles) were eluted at a 2Bv/h flow (1 l/h).

At the end the resin was washed with 50 g of demineralized water.

A gabapentin hydrochloride solution (792 g having gabapentin=10.3%, corresponding to 79.3 g) was charged at the same flow rate.

The resin was washed until pH 6-7 with approximately 1500 g of demineralized water.

Then, the product was eluted with 643 g of a 3% ammonia solution, followed by approximately 1550 g of demineralized water to wash the resin until neutrality.

The eluate fractions containing gabapentin were collected by obtaining a solution on which an HPLC assay was performed (gabapentin content 72.7 g).

2.4 g of 31% solution of hydrochloric acid were added thereto and the resulting solution was concentrated in vacuo at not more than 45° C. to obtain a residue having 33% of water content.

This crude product was diluted with methanol (45 g) and heated to 50° C. for 30 minutes. 189 g of isopropanol were added, the mixture was maintained at 50° C. for 30 minutes and then cooled to −5° C. in three hours.

The product was filtered off and washed to obtain 67.4 g of pure gabapentin (99.6% HPLC assay) in 85% yield.

The invention claimed is:

1. A process for the preparation of gabapentin comprising passage of a salt of gabapentin through a column comprising an ionic exchange resin of strong cationic type, elution of the gabapentin which has fixed onto the column, crystallization from organic solvent, and regeneration of the ionic exchange resin, wherein regeneration is carried out, in order, as follows:
   a. by partially regenerating the resin by treating the resin with an aqueous regenerating solution of inorganic acid in a quantity equal to a percentage of resin moles of from 50 to 90% of the theoretical percentage required for complete regeneration of the resin;
   b. by adding demineralized water in a quantity sufficient to separate the regenerating solution from the solution of a gabapentin salt of item c.;
   c. by adding a solution of gabapentin salt and by completing the resin regeneration through the acid released by fixing the gabapentin salt to the resin;
   d. by eluting the gabapentin which has fixed to the resin by using a base.

2. A process according to claim 1 wherein the partial regeneration of the ionic exchange resin of strong cationic type is carried out by using an aqueous solution of inorganic acid in a quantity equal to a percentage of the resin moles around 70-80%.

3. A process according to claim 1 wherein the partial regeneration is carried out by using an aqueous solution of an inorganic acid selected from the group consisting of hydrochloric, nitric and sulfuric acid.

4. A process according to claim 3 wherein the partial regeneration is carried out with an aqueous solution of hydrochloric acid.

5. A process according to claim 4 wherein the aqueous solution of hydrochloric acid has a concentration of from 5 to 10%.

6. A process according to claim 5 wherein the aqueous solution of hydrochloric acid has a concentration around 6%.

7. A process according to claim 1 wherein the partial regeneration of the ionic exchange resin of strong cationic type is carried out by using an aqueous solution of inorganic acid corresponding to the anion of the added gabapentin salt.

8. A process according to claim 1 wherein the elution of the gabapentin which has fixed to the resin is carried out by using an aqueous solution of ammonia.

9. A process according to claim 1 wherein the elution of the gabapentin which has fixed to the resin is carried out by using an aqueous solution of ammonia and alkaline hydroxide.

10. A process according to claim 9 wherein the alkaline hydroxide is sodium hydroxide.

11. A process according to claim 10 wherein the aqueous solution of ammonia and sodium hydroxide is obtained by mixing an aqueous solution of 3-4% ammonia and an aqueous solution of 7-8% sodium hydroxide.

12. A process according to claim 11 wherein the molar ratio of ammonia to sodium hydroxide is from 1:1 to 1:2.

13. A regeneration process comprising regeneration of a strong cationic exchange resin used in the purification of a gabapentin salt, which regeneration is carried out, in order, as follows:
   a. the partial regeneration of the resin by treatment of the resin with an aqueous regeneration solution of inorganic acid in a quantity equal to a percentage of resin moles of from 50 to 90% of the theoretical percentage required for complete regeneration of the resin;
   b. the addition of demineralized water in a quantity sufficient to separate the regeneration solution from the solution of a gabapentin salt of item c.;
   c. the addition of a solution of a gabapentin salt and the completion of the resin regeneration through the acid released by fixing the gabapentin salt to the resin.

14. A process according to claim 13 wherein the partial regeneration of the strong cationic exchange resin is carried out by using an aqueous solution of inorganic acid in a quantity equal to a percentage of resin moles around 70-80%.

15. A process according to claim 13, wherein the partial regeneration is carried out by using an aqueous solution of an inorganic acid selected from the group consisting of hydrochloric, nitric and sulfuric acid.

16. A process according to claim 15, wherein the regeneration is carried out with an aqueous solution of hydrochloric acid.

17. A process according to claim 16, wherein the aqueous solution of hydrochloric acid has a concentration of from 5 to 10%.

18. A process according to claim 17, wherein the aqueous solution of hydrochloric acid has a concentration around 6%.

19. The process for the preparation of gabapentin according to claim 4, wherein the salt of gabapentin is gabapentin hydrochloride.

20. A process according to claim 19, wherein the partial regeneration of the ionic exchange resin of strong cationic type is carried out by using an aqueous solution of hydrochloric acid in a quantity equal to a percentage of the resin moles around 70-80%.

21. A process according to claim 19, wherein the elution of the gabapentin which has fixed to the resin is carried out by using an ammonia aqueous solution.

22. A process according to claim 19, wherein the elution of the gabapentin which has fixed to the resin is carried out by using an aqueous solution of ammonia and alkaline hydroxide.

23. A process according to claim 19, wherein the aqueous solution of hydrochloric acid has a concentration of from 5 to 10%.

24. A process according to claim 23, wherein the aqueous solution of hydrochloric acid has a concentration around 6%.

* * * * *